US009216006B2

(12) United States Patent
Kuwabara

(10) Patent No.: US 9,216,006 B2
(45) Date of Patent: Dec. 22, 2015

(54) RADIOGRAPH ACQUISITION DEVICE, RADIOGRAPHIC IMAGING SYSTEM, AND RADIOGRAPHIC IMAGING METHOD

(75) Inventor: Takeshi Kuwabara, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 444 days.

(21) Appl. No.: 13/582,301

(22) PCT Filed: Feb. 24, 2011

(86) PCT No.: PCT/JP2011/054077
§ 371 (c)(1),
(2), (4) Date: Aug. 31, 2012

(87) PCT Pub. No.: WO2011/108426
PCT Pub. Date: Sep. 9, 2011

(65) Prior Publication Data
US 2012/0328078 A1  Dec. 27, 2012

(30) Foreign Application Priority Data

Mar. 1, 2010  (JP) .................. 2010-044339

(51) Int. Cl.
A61B 6/00 (2006.01)
H01L 27/146 (2006.01)
(Continued)

(52) U.S. Cl.
CPC ............... *A61B 6/545* (2013.01); *A61B 6/4014* (2013.01); *A61B 6/4233* (2013.01); *A61B 6/4266* (2013.01); *A61B 6/4411* (2013.01); *G01V 5/104* (2013.01); *H01L 27/14658* (2013.01); *H04N 5/32* (2013.01); *A61B 6/4283* (2013.01); *A61B 6/4494* (2013.01); *A61B 6/5258* (2013.01);
(Continued)

(58) Field of Classification Search
CPC .... A61B 6/545; A61B 6/4014; A61B 6/4233; A61B 6/4266; A61B 6/4411; H01L 27/14658; H04N 5/32
See application file for complete search history.

(56) References Cited

U.S. PATENT DOCUMENTS 6,504,897 B1    1/2003  Yonekawa
8,731,141 B2 *  5/2014  Kuwabara ..................... 378/116
(Continued)

FOREIGN PATENT DOCUMENTS

DE  102007035625 A1  2/2009
JP  4-364834 A       12/1992
JP  2001-149358 A     6/2001
(Continued)

OTHER PUBLICATIONS

Chinese Office Action and Search Report with English translation thereof, dated Mar. 31, 2014, for Chinese Application No. 201180011753.7.
(Continued)

Primary Examiner — Jack Berman
(74) Attorney, Agent, or Firm — Birch, Stewart, Kolasch & Birch, LLP

(57) ABSTRACT

The disclosed radiograph acquisition device has: a selection unit that selects one radiation detection device from among a plurality of radiation detection devices that can convert radiation to radiographs; and an acquisition unit that acquires the radiograph of one radiation detection device when radiation is radiated at a subject, and the radiograph of at least one other radiation detection device aside from the one radiation device among the plurality of radiation detection devices.

9 Claims, 6 Drawing Sheets

(51) Int. Cl.
*H04N 5/32* (2006.01)
*G01V 5/10* (2006.01)

(52) U.S. Cl.
CPC ............... *A61B6/563* (2013.01); *A61B 6/566* (2013.01); *A61B 6/586* (2013.01)

(56) References Cited

U.S. PATENT DOCUMENTS

2004/0071263 A1    4/2004  Motoki
2011/0317809 A1    12/2011 Eguchi

FOREIGN PATENT DOCUMENTS

| | | |
|---|---|---|
| JP | 2002-44413 A | 2/2002 |
| JP | 2003-172783 A | 6/2003 |
| JP | 2004-73462 A | 3/2004 |
| JP | 2004-73463 A | 3/2004 |
| JP | 2005-13397 A | 1/2005 |
| JP | 2006-25828 A | 2/2006 |
| JP | 2007-82650 A | 4/2007 |
| JP | 2008-132216 A | 6/2008 |
| JP | 2009-18208 A | 1/2009 |
| JP | 2009-219586 A | 10/2009 |
| JP | 2010-29419 A | 2/2010 |
| WO | WO 2010/073894 A1 | 7/2010 |

OTHER PUBLICATIONS

Japanese Office Action for corresponding Japanese Application 2010-044339, dated Nov. 12, 2013 with English translation.
Japanese Office Action for corresponding Japanese Application No. 2010-044339 dated Jul. 30, 2013 (with partial English translation).
Japanese Office Action dated Apr. 7, 2015 issued in corresponding JP Application No. 2010-044339 with an English translation of the pertinent portion.

* cited by examiner

RADIOGRAPH ACQUISITION DEVICE, RADIOGRAPHIC IMAGING SYSTEM, AND RADIOGRAPHIC IMAGING METHOD

TECHNICAL FIELD

The present invention relates to a radiographic image capturing system (radiographic imaging system) and a radiographic image capturing method (radiographic imaging method) for applying radiation to a subject and converting radiation that has passed through the subject into a radiographic image with a radiation detecting device. The present invention also concerns a radiographic image acquiring apparatus (radiograph acquisition device) for acquiring a radiographic image from a radiation detecting device.

BACKGROUND ART

In the medical field, it has widely been customary to apply radiation to a subject, to convert radiation that has passed through the subject into a radiographic image with a radiation conversion panel, and to acquire the radiographic image from the radiation conversion panel. One known form of radiation conversion panel is a stimulable phosphor panel for storing radiation energy representing a radiographic image in a phosphor, and retrieving the radiographic image as stimulated light emitted in response to application of stimulating light thereto. The stimulable phosphor panel is supplied to a radiographic image acquiring apparatus, which performs a process of acquiring the radiographic image in order to obtain the radiographic image as a visible image.

In operating rooms or the like, it is necessary to immediately read radiographic images from radiation conversion panels, which have captured the radiographic images, and to display the radiographic images in order to treat subjects (patients) quickly and properly. Radiation conversion panels that have been developed to meet such requirements include a direct-conversion-type radiation detector, which employs a solid-state detector for converting radiation directly into electric signals, and an indirect-conversion-type radiation detector, which employs a scintillator for converting radiation into visible light and a solid-state detector for converting the visible light into electric signals.

Certain medical organizations incorporate a radiographic image capturing system having a plurality of radiation detecting devices with radiation conversion panels employed therein (see Japanese Laid-Open Patent Publication No. 2004-073462 and Japanese Laid-Open Patent Publication No. 2009-219586).

It may be assumed that all of the radiation detecting devices of such a radiographic image capturing system include therein direct-conversion-type or indirect-conversion-type radiation conversion panels (hereinafter referred to as "FPDs" (Flat Panel Detectors)). A process of applying radiation to a subject and acquiring a radiographic image of the subject from such radiation conversion panels will be described below.

First, a doctor or radiological technician selects one of the radiation detecting devices, and makes the FPD of the selected radiation detecting device ready to store electric signals (electric charges) converted from the radiation.

Then, the doctor or radiological technician places a subject (patient) between a radiation source and the selected radiation detecting device. When the radiation source applies radiation through the subject to the radiation detecting device, the FPD converts radiation that has passed through the subject into electric charges and stores the electric charges. After radiation has been applied to the radiation detecting device, the radiographic image acquiring apparatus acquires the electric charges stored in the FPD as a radiographic image representative of the subject.

SUMMARY OF INVENTION

With the radiographic image capturing system according to the background art, as described above, one radiation detecting device is selected, radiation is applied from the radiation source through the subject to the selected radiation detecting device, and the radiographic image acquiring apparatus acquires a radiographic image from the selected radiation detecting device. In this manner, the subject and the radiographic image are associated with each other.

If the selected radiation detecting device is in a certain state (e.g., if the selected radiation detecting device fails, or if the amount of electric power charged in a battery thereof is insufficient to capture a radiographic image, or if the selected radiation detecting device is physically spaced from the subject (in terms of distances, angles, and positions in relation to an image capturing base used in combination therewith) such that the selected radiation detecting device cannot be used, then the selected radiation detecting device is replaced with another radiation detecting device. If radiation is applied from the radiation source through the subject to the other radiation detecting device, the radiographic image generated by the other radiation detecting device is representative of the subject.

However, if the doctor or radiological technician forgets to indicate to the radiographic image acquiring apparatus that the radiation detecting devices have been changed in order to capture the radiographic image, then the radiographic image acquiring apparatus is likely to acquire the radiographic image from the selected radiation detecting device, and to associate the subject and the acquired radiographic image with each other. As a result, in a case that the radiographic image acquiring apparatus acquires the radiographic image from the selected radiation detecting device, since the acquired radiographic image does not represent the subject, the radiographic image acquiring apparatus judges the image capturing process as a failure, and indicates that a process for capturing a radiographic image of the subject should be applied again.

Stated otherwise, if a radiation detecting device (another radiation detecting device) having an FPD that is actually irradiated with radiation, and a radiation detecting device (a selected radiation detecting device) having an FPD from which the radiographic image is acquired are not the same as each other, then the radiographic image capturing system according to the background art does not acquire a radiographic image representative of the subject from the other radiation detecting device, but rather, performs another process for capturing a radiographic image of the subject again. Consequently, the radiographic image capturing system tends to expose the subject to radiation unnecessarily.

The present invention has been made in order to eliminate the above difficulties. It is an object of the present invention to provide a radiographic image acquiring apparatus, a radiographic image capturing system, and a radiographic image capturing method, which are capable of reliably acquiring a radiographic image representative of a subject while preventing the subject from being needlessly exposed to radiation.

A radiographic image acquiring apparatus according to the present invention comprises a selector for selecting one of a plurality of radiation detecting devices, each of which is capable of converting radiation into a radiographic image, and an acquirer for acquiring a radiographic image from the one radiation detecting device and a radiographic image from at least one other radiation detecting device that differs from the one radiation detecting device, from among the plurality of radiation detecting devices, in a case that a subject is irradiated with radiation.

A radiographic image capturing system according to the present invention comprises a plurality of radiographic image capturing apparatus including respective radiation sources each of which outputs radiation, and respective radiation detecting devices each of which converts the radiation into a radiographic image, and a radiographic image acquiring apparatus including a selector for selecting the radiation detecting device of one radiographic image capturing apparatus from among the radiation detecting devices of the plurality of radiographic image capturing apparatus, and an acquirer for acquiring a radiographic image from the one radiation detecting device and a radiographic image from at least one other radiation detecting device that differs from the one radiation detecting device, from among the radiation detecting devices of the plurality of radiographic image capturing apparatus, in a case that a subject is irradiated with radiation.

A method of capturing a radiographic image according to the present invention comprises the steps of selecting, with a selector, one of a plurality of radiation detecting devices, each of which is capable of converting radiation into a radiographic image, applying radiation to a subject, and acquiring, with an acquirer, a radiographic image from the one radiation detecting device and a radiographic image from at least one other radiation detecting device that differs from the one radiation detecting device, from among the plurality of radiation detecting devices.

According to the above invention, the acquirer acquires both a radiographic image from the one radiation detecting device selected by the selector, and a radiographic image from at least one other radiation detecting device that differs from the one radiation detecting device.

If radiation is applied through the subject to the one radiation detecting device, then the control device acquires a radiographic image from the one radiation detecting device, thereby acquiring a radiographic image representative of the subject. If radiation is applied through the subject to the other radiation detecting device, then the control device acquires a radiographic image from the other radiation detecting device, thereby acquiring a radiographic image representative of the subject.

More specifically, in a case that the one image capturing apparatus is changed over to the other image capturing apparatus in order to capture a radiographic image, it is desirable for the selector to select the other image capturing apparatus before the radiographic image has been captured. However, the other image capturing apparatus may not be selected for capturing a radiographic image, and hence, a radiographic image may not be acquired from the other image capturing apparatus. According to the present embodiment, regardless of whether or not the selector has selected the other image capturing apparatus, both a radiographic image from the one radiation detecting device and a radiographic image from the other radiation detecting device are acquired, thereby reliably acquiring a radiographic image representative of the subject.

According to the present embodiment, therefore, regardless of whether the one radiation detecting device or the other radiation detecting device is used to capture a radiographic image, the acquirer reliably acquires a radiographic image representative of the subject. As a result, the subject is prevented from being exposed to radiation unnecessarily.

The radiographic image acquiring apparatus may further comprise a judging section for judging whether or not the radiographic image from the one radiation detecting device is a significant radiographic image representative of the subject.

Therefore, it is possible to determine whether or not the radiographic image from the one radiation detecting device is a significant radiographic image representative of the subject. A significant radiographic image, which is representative of the subject, is a radiographic image represented by digital image data, an average luminance value or a variance luminance value of which is equal to or greater than a prescribed threshold value, for example.

The radiographic image acquiring apparatus may further comprise an indicating unit for externally indicating a judgment result from the judging section, if the judging section judges that the radiographic image from the one radiation detecting device is not the significant radiographic image.

Therefore, the doctor or radiological technician can easily recognize that an image capturing process has been carried out without requiring the selector to select the other radiation detecting device.

The judging section judges whether or not the radiographic image from the other radiation detecting device is the significant radiographic image, if the judging section judges that the radiographic image from the one radiation detecting device is not the significant radiographic image, thereby determining whether or not the radiographic image from the other radiation detecting device is the significant radiographic image.

The acquirer successively acquires radiographic images from other radiation detecting devices until the judging section has found the significant radiographic image, if the judging section judges that the radiographic image from the one radiation detecting device is not the significant radiographic image.

The selector selects the one radiation detecting device and designates an imaging method to be carried out upon application of radiation to the subject using the one radiation detecting device, and the acquirer acquires a radiographic image preferentially from a radiation detecting device, from among the other radiation detecting devices, which produces a radiographic image according to the imaging method, or acquires a radiographic image preferentially from another radiation detecting device that is in close proximity to the one radiation detecting device.

If the one radiation detecting device is not used, but rather another radiation detecting device is used to capture a radiographic image, then it is assumed it is highly likely to have captured a radiographic image using another radiation detecting device, according to the same imaging method as the imaging method (e.g., an upright imaging process or a supine imaging process) of the one radiation detecting device, or to have captured a radiographic image using another radiation detecting device that is closest in proximity to the one radiation detecting device. It is thus possible to acquire a radiographic image preferentially from another radiation detecting device according to the same imaging method, or from another radiation detecting device that is closest in proximity to the one radiation detecting device, thereby making it possible to acquire a significant radiographic image quickly and reliably.

The radiographic image acquiring apparatus may further comprise a switcher for switching selection of the one radiation detecting device to selection of the other radiation detecting device, if the judging section judges that the radiographic image from the other radiation detecting device is the significant radiographic image.

Since a next imaging cycle may be carried out using the other radiation detecting device, which has produced a significant radiographic image, the switcher automatically switches from selection of the one radiation detecting device to selection of the other radiation detecting device, thereby preventing the other radiation detecting device from being unselected due to an oversight in a subsequent image capturing cycle.

The radiographic image acquiring apparatus preferably further comprises an output unit for externally outputting the radiographic image, which the judging section has judged as being the significant radiographic image.

The doctor can thus interpret a significant radiographic image for facilitating diagnosis.

In a case that radiation is applied to the subject in an image capturing chamber, the acquirer acquires the radiographic image from the one radiation detecting device and the radiographic image from the other radiation detecting device, which also is present in the image capturing chamber, from among the plurality of radiation detecting devices.

Inasmuch as a radiographic image is acquired from the radiation detecting device that is present in the image capturing chamber, it is possible to reliably prevent image acquiring processes from being performed needlessly on radiation detecting devices that are present outside of the image capturing chamber, while also efficiently carrying out a process of acquiring radiographic images.

The radiographic image acquiring apparatus further comprises an identification information storage unit for storing identification information of the plurality of radiation detecting devices that are present in an image capturing chamber in a case that radiation is applied to the subject in the image capturing chamber, wherein the acquirer acquires radiographic images from the plurality of radiation detecting devices that are present in the image capturing chamber based on the identification information stored in the identification information storage unit.

Inasmuch as radiographic images are acquired only from radiation detecting devices that are present in the image capturing chamber, it is possible to reliably prevent image acquiring processes from being performed in error on radiation detecting devices that are present outside of the image capturing chamber, while also efficiently carrying out the process of acquiring radiographic images.

Preferably, each of the radiation detecting devices comprises a radiation conversion panel for converting radiation into electric charges, storing the electric charges, and outputting the stored electric charges as an electric signal to an external device. The radiation conversion panel is made ready to store electric charges before radiation is applied to the subject.

It is not necessary to irradiate the radiation detecting devices with triggering radiation in order to instruct the radiation conversion panel to store electric charges prior to a main image capturing process. Therefore, the arrangement for instructing the storage of electric charges is simplified, and the dose of radiation to which the subject is exposed can be reduced.

According to the present invention, regardless of whether the one radiation detecting device or the other radiation detecting device is used to capture a radiographic image, the acquirer reliably acquires a radiographic image representative of the subject. As a result, the subject is prevented from being exposed to radiation needlessly.

DESCRIPTION OF EMBODIMENTS

A radiographic image capturing system incorporating a radiographic image acquiring apparatus according to an embodiment of the present invention will be described below with reference to FIGS. 1 through 6, in relation to a radiographic image capturing method carried out by the radiographic image capturing system.

Figure 1:
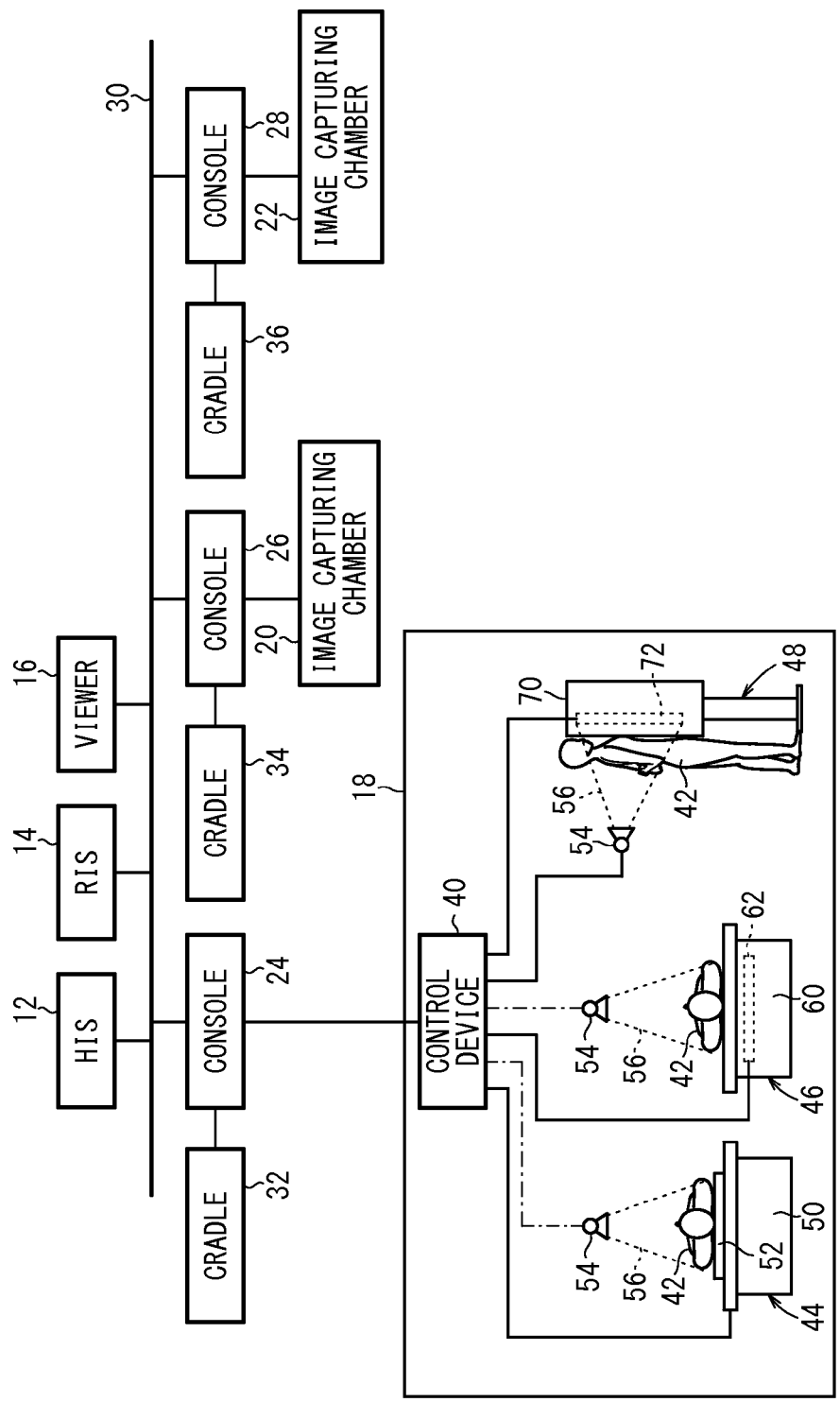
FIG. 1 is a block diagram of a radiographic image capturing system according to an embodiment of the present invention.

As shown in FIG. 1, a radiographic image capturing system 10 according to the present embodiment includes a medical information system 12 (HIS: Hospital Information System) for managing medical procedures in a hospital, a radiological information system 14 (RIS) for managing a process of capturing radiographic images in a radiological department, a viewer 16 which a doctor uses to make a diagnosis based on the interpretation of radiographic images, and consoles 24, 26, 28 disposed in respective processing chambers, which are located respectively adjacent to a plurality of image capturing chambers 18, 20, 22 of the radiological department, for managing and controlling respective image capturing apparatus 44, 46, 48 having different specifications. The HIS 12, the RIS 14, the viewer 16, and the consoles 24, 26, 28 are interconnected via an in-hospital network 30. In the processing chambers, respective cradles 32, 34, 36 are disposed for charging radiation detecting devices 52, 62, 72 connected respectively to the consoles 24, 26, 28.

The image capturing chamber 18 houses therein image capturing apparatus 44, 46 for capturing images of subjects 42 in a supine position (supine imaging process), an image capturing apparatus 48 for capturing an image of a subject 42 in an upright position (upright imaging process), and a control device (acquirer) 40 interconnecting the console 24 and the image capturing apparatus 44, 46, 48. Each of the other image capturing chambers 20, 22 also houses therein the control device 40 and the image capturing apparatus 44, 46, 48, although such devices have been omitted from illustration in FIG. 1. The consoles 24, 26, 28 and the corresponding control devices 40 jointly make up a radiographic image acquiring apparatus according to the present embodiment.

The image capturing apparatus 44 has an image capturing base 50 and a radiation detecting device 52 placed on the image capturing base 50. The image capturing apparatus 46 has an image capturing base 60 and a radiation detecting device 62 placed in the image capturing base 60. The image capturing apparatus 48 has an upright image capturing base 70 and a radiation detecting device 72 placed in the image capturing base 70. The image capturing apparatus 44, 46, 48 share a single radiation source 54. When the radiation source 54 applies radiation 56 to the subject 42, the irradiated radiation detecting device converts the radiation 56, which has passed through the subject 42, into a radiographic image representative of the subject 42, whereas the other two radiation detecting devices produce radiographic images that are not representative of the subject 42.

In the image capturing apparatus 44, the radiation detecting device 52 is not housed in the image capturing base 50. The image capturing apparatus 44 is not limited to performing the supine imaging process illustrated in FIG. 1, but may also capture an image of a desired region (legs or the like) of the subject 42 while the subject 42 sits on the image capturing base 50, for example. In FIG. 1, the control device 40 and the image capturing apparatus 44, 46, 48 are illustrated as being interconnected by wired links. However, the control device 40 and the image capturing apparatus 44, 46, 48 may be interconnected via wireless links. In FIG. 1, the radiation detecting devices 52, 62, 72 are disposed respectively in the image capturing apparatus 44, 46, 48. According to the present embodiment, however, at least two radiation detecting devices may be disposed in the image capturing apparatus 44, 46, 48. In such a case, one of the three image capturing apparatus 44, 46, 48, which is free of a radiation detecting device, may utilize the radiation detecting device of one of the other image capturing apparatus.

Figure 2:
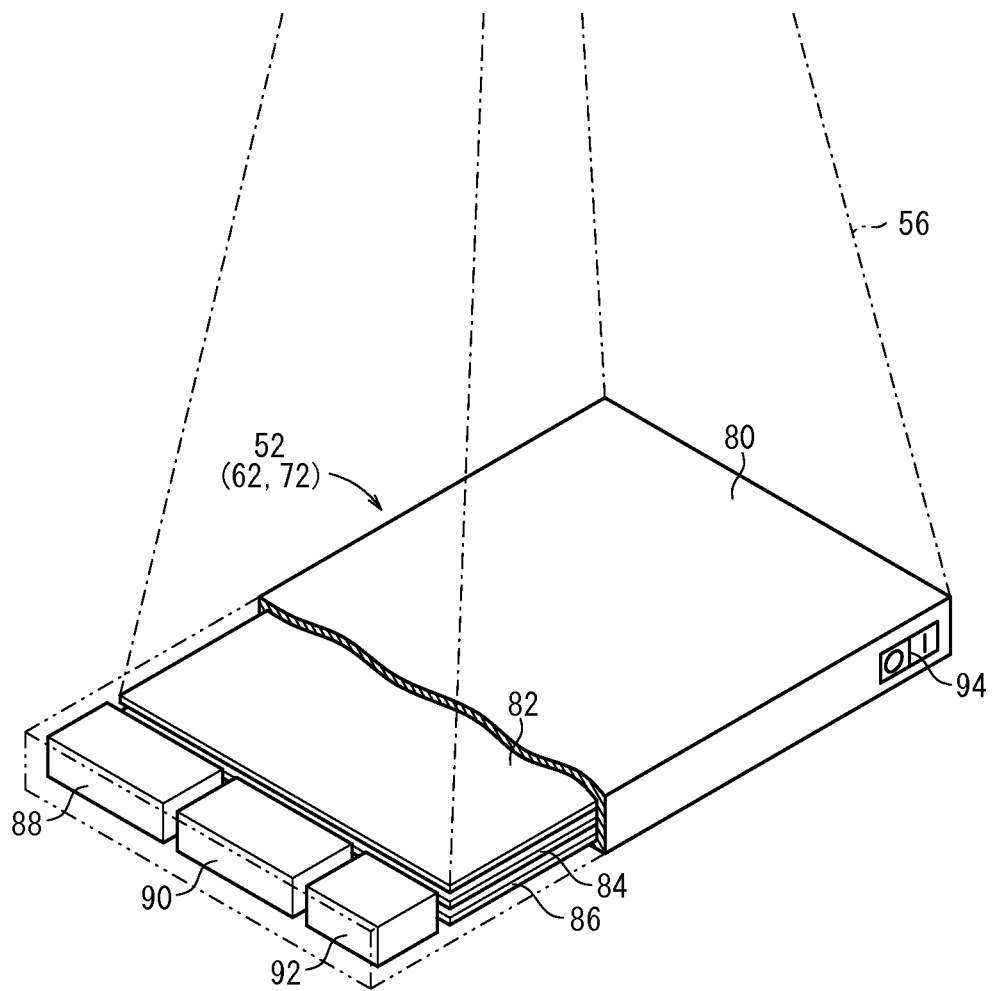
FIG. 2 is a schematic view of a radiation detecting device.

As shown in FIG. 2, each of the radiation detecting devices 52, 62, 72 employed by the image capturing apparatus 44, 46, 48 has a casing 80 made of a material that is permeable to radiation 56. The casing 80 houses therein a grid 82 for removing scattered rays of radiation 56 from the subject 42 (see FIG. 1), a radiation conversion panel 84 for converting radiation 56 that has passed through the subject 42 into electric image information, and a lead plate 86 for absorbing back scattered rays of radiation 56. The grid 82, the radiation conversion panel 84, and the lead plate 86 are successively arranged from an irradiated surface of the casing 80 toward a bottom surface of the casing 80. The irradiated surface of the casing 80 may be constructed as the grid 82.

The radiation conversion panel 84, which is in the form of a planar radiation detector (FPD), comprises a direct-conversion-type radiation detector for detecting and converting radiation 56 directly into electric charges and storing the electric charges, or an indirect-conversion-type radiation detector for converting radiation 56 into visible light, converting the visible light into electric charges, and storing the electric charges. It is assumed hereinafter that the radiation conversion panel 84 comprises an indirect-conversion-type radiation detector.

The casing 80 also houses therein a battery 88, which serves as a power supply for the radiation conversion panel 84, a controller 90 for energizing the radiation conversion panel 84 with electric power supplied from the battery 88, and a transceiver 92 for sending a radiographic image of the subject 42, which is represented by electric charges stored in the radiation conversion panel 84, via the control device 40 (see FIG. 1) to the consoles 24, 26, 28. The casing 80 has on a side thereof a power supply switch 94 for activating the radiation detecting device 52, 62, 72.

Figure 3:
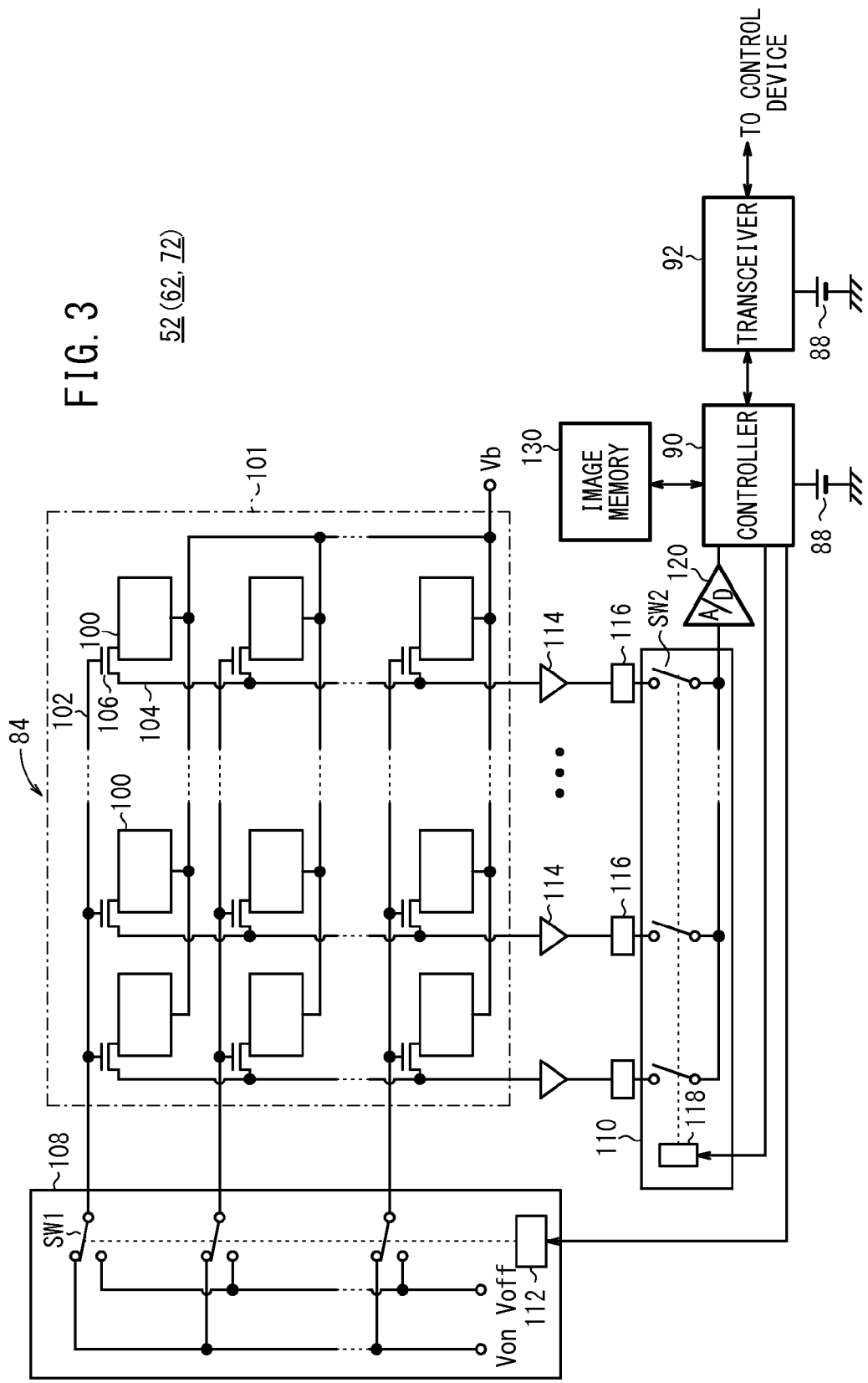
FIG. 3 is a circuit diagram of the radiation detecting device shown in FIG. 2.

A circuit arrangement inside the radiation detecting device 52, 62, 72 will be described below with reference to FIG. 3.

The radiation conversion panel 84 comprises an array of TFTs 106 arranged in rows and columns, and a photoelectric conversion layer 101 made of a material such as amorphous silicon (a-Si) or the like, and having solid-state detectors (hereinafter referred to as pixels) 100 provided thereon for converting visible light into electric signals, the photoelectric conversion layer 101 being disposed on the array of TFTs 106. The pixels 100, which are supplied with a bias voltage Vb from the battery 88, store electric charges generated by conversion of visible light into electric signals (analog signals). The TFTs 106 are turned on along each row at a time to read the electric charges as an image signal.

The TFTs 106 connected to the respective pixels 100 are connected to respective gate lines 102 that extend parallel to the rows, and to respective signal lines 104 that extend parallel to the columns. The gate lines 102 are connected to a line scanning driver 108, and the signal lines 104 are connected to a multiplexer 110. The gate lines 102 are supplied with control signals Von, Voff for turning on and off the TFTs 106 along the rows from the line scanning driver 108. The line scanning driver 108 comprises a plurality of first switches SW1 for switching between the gate lines 102, and an address decoder 112 for outputting a selection signal for selecting one of the first switches SW1 at a time. The address decoder 112 is supplied with an address signal from the controller 90.

The signal lines 104 are supplied with electric charges stored in the pixels 100 through the TFTs 106 arranged in the columns. The electric charges supplied to the signal lines 104 are amplified by amplifiers 114. The amplifiers 114 are connected through respective sample and hold circuits 116 to the multiplexer 110. The multiplexer 110 comprises a plurality of second switches SW2 for successively switching between the signal lines 104, and an address decoder 118 for outputting a selection signal for selecting one of the second switches SW2 at a time. The address decoder 118 is supplied with an address signal from the controller 90. The multiplexer 110 is connected to an A/D converter 120. A radiographic image signal is converted by the A/D converter 120 into a digital image signal, which is supplied to the controller 90. The controller 90 stores the radiographic image signal as a digital image signal in an image memory 130, or alternatively, sends the radiographic image signal stored in the image memory 130 through the transceiver 92 to the control device 40.

The TFTs 106, which function as switching elements, may be combined with any of various other image capturing devices such as a CMOS (Complementary Metal-Oxide Semiconductor) image sensor, or may be replaced with a CCD (Charge-Coupled Device) image sensor, in which electric charges are shifted and transferred by shift pulses that correspond to gate signals used in the TFTs 106.

Figure 4:
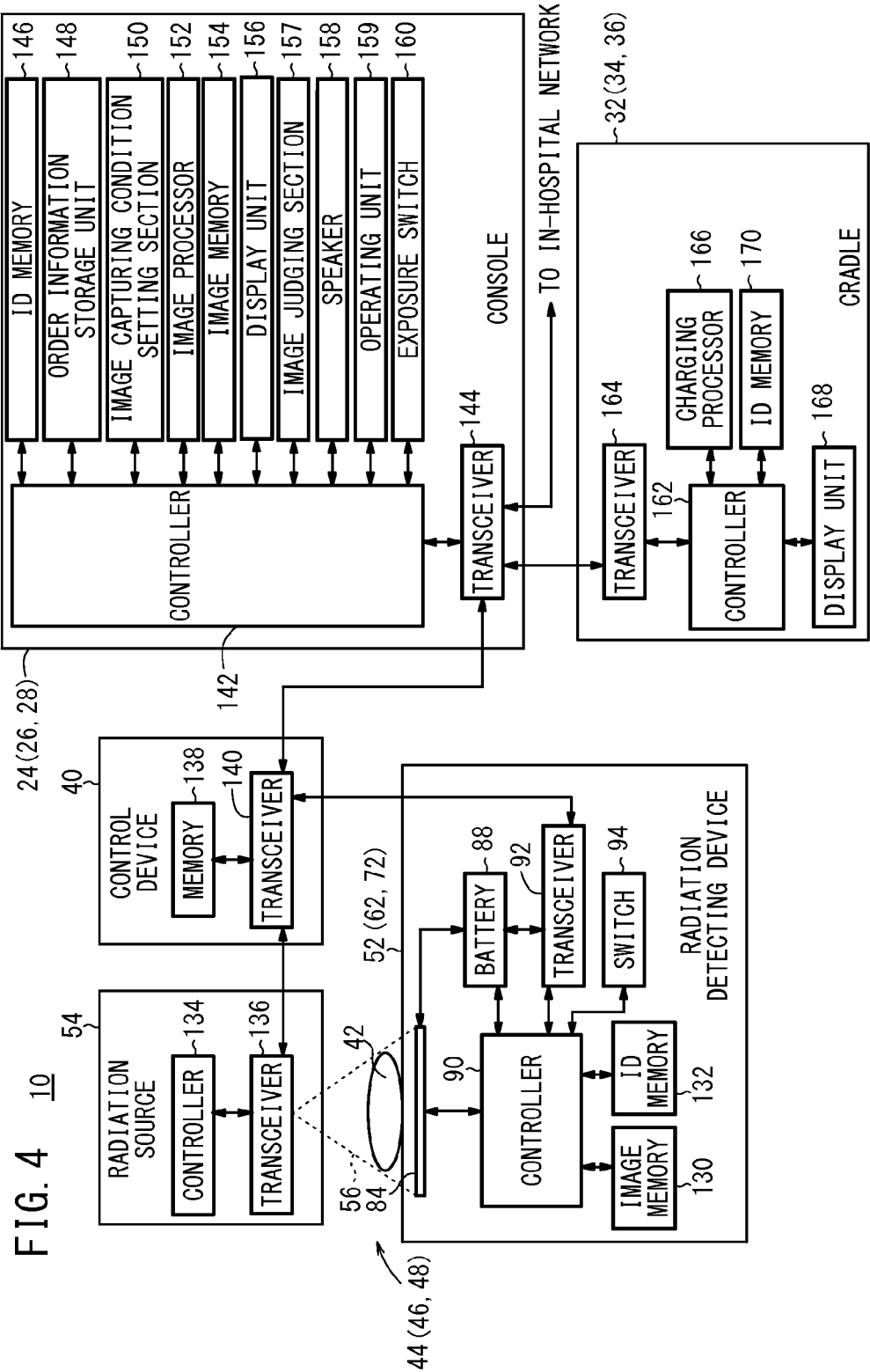
FIG. 4 is a detailed block diagram of the radiographic image capturing system shown in FIG. 1.

FIG. 4 is a detailed block diagram of the radiographic image capturing system 10. Components of the radiographic image capturing system 10, which have not been described with reference to FIGS. 1 through 3, will primarily be described below.

Each of the radiation detecting devices 52, 62, 72 has an ID memory 132 storing therein ID information for identifying a particular radiation detecting device. The controller 90 performs a calibration process (a process of correcting brightness, darkness, and defects in the radiographic images) on the radiation conversion panel 84, either periodically or upon activation of the radiation detecting devices 52, 62, 72, and stores various tables generated by the calibration process for brightness, darkness, and defect correction in the image memory 130. The calibration process that is carried out is a known process (see, for example, Japanese Laid-Open Patent Publication No. 2009-028373).

The radiation source 54 has a controller 134 for controlling the radiation source 54 to emit radiation 56, and a transceiver 136 for sending signals to and receiving signals from the control device 40.

The control device 40 has a memory 138 for storing the various tables referred to above, and a transceiver 140 for sending signals to and receiving signals from the transceivers 92 of the radiation detecting devices 52, 62, 72, the transceiver 136 of the radiation source 54, and the consoles 24, 26, 28. The transceiver 140 sends radiation image signals acquired from the image memory 130 via the controller 90 and the transceiver 92 to the consoles 24, 26, 28.

Each of the consoles 24, 26, 28 has a controller 142, a transceiver 144, an ID memory (identification information storage unit) 146, an order information storage unit 148, an image capturing condition setting section 150, an image processor 152, an image memory 154, a display unit (output unit, indicating unit) 156, an image judging section (judging section, switcher) 157, a speaker (indicating unit) 158, an operating unit (selector, switcher) 159, and an exposure switch 160.

The transceiver 144 sends signals to and receives signals from the HIS 12, the RIS 14, the viewer 16, and the other consoles via the in-hospital network 30, and also sends signals to and receives signals from the control device 40 and the cradles 32, 34, 36.

The controllers 142 of the consoles 24, 26, 28 control components in each of the respective consoles 24, 26, 28.

Each of the controllers 142 stores image capturing order information acquired from the RIS 14 in the order information storage unit 148. The controller 142 also stores image capturing conditions for the image capturing apparatus 44, 46, 48, which have been acquired from the RIS 14, or which have been set by the doctor or radiological technician by operating the operating unit 159 such as a keyboard, a mouse, or the like, in the image capturing condition setting section 150.

The order information is generated by the doctor using the RIS 14. The order information includes patient information for identifying the patient, such as the name, age, gender, etc., of the patient, an image capturing apparatus to be used to capture a radiographic image, a body region to be imaged, an imaging method such as a supine imaging process or an upright imaging process, and image capturing conditions. The image capturing conditions refer to conditions for determining a dose of radiation to be applied to the subject 42, e.g., a tube voltage and a tube current of the radiation source 54, an irradiation time of the radiation 56, etc.

The doctor or radiological technician operates the operating unit 159 in order to select one of the three image capturing apparatus 44, 46, 48, which are present in the respective image capturing chambers 18, 20, 22, as an image capturing apparatus to be used to capture radiographic images, as well as to select an imaging method for the selected image capturing apparatus, and to enter the ID information (identification information) of a radiation detecting device (one radiation detecting device) to be used by the selected image capturing apparatus. The controller 142 sets the selected image capturing apparatus and the selected imaging method, which are included in the image capturing conditions, in the image capturing condition setting section 150.

The doctor or radiological technician operates the operating unit 159 in order to enter, in addition to the ID information of the radiation detecting device used by the selected image capturing apparatus, the ID information of all of the radiation detecting devices 52, 62, 72 that are present in the image capturing chambers 18, 20, 22, as well as the ID information of any radiation detecting devices that are currently being charged by the cradle connected to the selected image capturing apparatus. The entered ID information is stored in the ID memory 146. In addition to the ID information referred to above, the ID memory 146 may store ID information of all of the radiation detecting devices that are owned by the hospital. Instead of entering ID information through the operating unit 159, bar codes representative of the ID information may be applied to the respective radiation detecting apparatus, and such bar codes may be read by a bar-code reader, not shown, in order to store the ID information of the radiation detecting apparatus in the ID memory 146.

In the event that the doctor or radiological technician turns on the exposure switch 160, the controller 142 outputs to the control device 40 the image capturing conditions that are set in the image capturing condition setting section 150, and the ID information, which is stored in the ID memory 146, of all of the radiation detecting devices 52, 62, 72 in the selected image capturing chamber.

In accordance with the image capturing conditions and the ID information, which are input to the control device 40, the control device 40 activates the radiation detecting devices 52, 62, 72 of the respective image capturing apparatus 44, 46, 48 in the selected image capturing chamber, regardless of whether or not the power supply switch 94 has been turned on, thereby supplying the bias voltage Vb from the battery 88 to the radiation conversion panel 84 to ready the pixels 100 for storage of electric charges therein.

In a state where the radiation conversion panel 84 of each of the radiation detecting devices 52, 62, 72 of the respective image capturing apparatus 44, 46, 48 is ready to store electric charges therein, the control device 40 controls the radiation source 54 so as to emit radiation 56.

After radiation 56 has been applied to the subject 42 (i.e., after a radiographic image of the subject 42 has been captured), the control device 40 successively acquires radiographic images obtained by the radiation detecting devices 52, 62, 72, including the radiographic image obtained by the one radiation detecting device, and sends the acquired radiographic images to the consoles 24, 26, 28.

More specifically, the control device 40 initially acquires a radiographic image obtained by the one radiation detecting device, and outputs the acquired radiographic image to the consoles 24, 26, 28. Thereafter, the control device 40 preferentially acquires a radiographic image obtained by another radiation detecting device, which is close in proximity to the one radiation detecting device, and outputs the acquired radiographic image to the consoles 24, 26, 28. Alternatively, the control device 40 may acquire a radiographic image obtained by the one radiation detecting device, and send the acquired radiographic image to the consoles 24, 26, 28. Thereafter, the control device 40 may preferentially acquire a radiographic image obtained by another radiation detecting device, the imaging method of which is the same as the one radiation detecting device, and sends the acquired radiographic image to the consoles 24, 26, 28.

While the control device 40 is successively acquiring radiographic images obtained by the radiation detecting devices 52, 62, 72, if the image judging section 157 finds a significant (effective) radiographic image representative of the subject 42, then the control device 40 immediately stops the process of acquiring radiographic images.

While radiographic images are successively being input by the control device 40 from the radiation detecting devices 52, 62, 72 to the consoles 24, 26, 28, the image judging section 157 judges whether or not there is a significant radiographic image representative of the subject 42.

More specifically, the image judging section 157 judges whether or not the radiographic image obtained by the one radiation detecting device is a significant radiographic image representative of the subject 42. A significant radiographic image representative of the subject 42 is typified by a radiographic image, which is represented by digital image data the average luminance value or variance luminance value of which is equal to or greater than a prescribed threshold value, for example. More specifically, if the radiographic image represented by digital image data includes a white area representative of the subject 42 because the subject 42 absorbs a portion of the radiation 56, then the average luminance value or variance luminance value of the image data is considered to be relatively high. Therefore, the image judging section 157 judges image data, the average luminance value or variance luminance value of which is equal to or greater than the threshold value, as a significant radiographic image representative of the subject 42. The average luminance value or variance luminance value may be an average or variance value of the entire image data, or an average or variance value of a particular area of the image data that is representative of the subject 42.

If the image judging section 157 determines that the radiographic image obtained by the one radiation detecting device is a significant radiographic image, then the image judging section 157 causes the control device 40 to cancel the process of acquiring radiographic images, and outputs the radiographic image obtained by the one radiation detecting device to the image processor 152. The image processor 152 processes the radiographic image, and the display unit 156 displays the processed radiographic image.

If the image judging section 157 determines that the radiographic image obtained by the one radiation detecting device is not a significant radiographic image, and further determines that the radiographic image obtained by another radiation detecting device is a significant radiographic image, then the image judging section 157 causes the control device 40 to cancel the process of acquiring radiographic images, and warns (notifies) the doctor or radiological technician via the speaker 158 and/or the display unit 156 that a radiographic image of the subject 42 has been captured using a radiation detecting device (another radiation detecting device) other than the radiation detecting device (one radiation detecting device) set in the image capturing conditions.

At the same time that the image judging section 157 provides the warning through the speaker 158 and/or the display unit 156, the image judging section 157 may output the radiographic image obtained by the other radiation detecting device to the image processor 152, so that the display unit 156 may display the processed radiographic image.

If the image judging section 157 determines that neither one of the radiographic image obtained by the one radiation detecting device or the radiographic image obtained by another radiation detecting device is a significant radiographic image, then the image judging section 157 judges whether or not the radiographic image obtained by still another radiation detecting device is a significant radiographic image. If the radiographic image is a significant radiographic image, then the image judging section 157 warns the doctor or radiological technician again via the speaker 158 and/or the display unit 156, and outputs the radiographic image obtained by the still other radiation detecting device to the image processor 152, whereupon the display unit 156 displays the processed radiographic image.

In other words, in the case that there are a plurality of other radiation detecting devices in the image capturing chambers 18, 20, 22, the control device 40 successively acquires radiographic images from the other radiation detecting devices, and then sends the acquired radiographic images to the consoles 24, 26, 28 until the image judging section 157 finds a significant radiographic image.

If the image judging section 157 determines that the radiographic image obtained by another radiation detecting device is a significant radiographic image, then the image judging section 157 assumes that the subject 42 should be irradiated with radiation 56 using the other radiation detecting device in a next imaging cycle, and replaces (switches from) the image capturing conditions, which are presently set in the image capturing condition setting section 150, including the image capturing apparatus (one radiation detecting device), the imaging method, and the ID information, with (to) the image capturing conditions including the image capturing apparatus, the imaging method, and the ID information, which correspond to the other radiation detecting device.

It has been described above that the image judging section 157 judges whether or not the image data represent a significant radiographic image representative of the subject 42 based on the average luminance value or variance luminance value of the image data. However, the image judging section 157 may judge whether or not the image data represent a significant radiographic image representative of the subject 42 based on an average density value or variance density value of the image data. More specifically, if a radiographic image, which is represented by image data, includes a white area representative of the subject 42 because the subject 42 absorbs a portion of the radiation 56, the average density value or variance density value of the image data is considered to be relatively low. Therefore, the image judging section 157 may judge image data, the average density value or variance density value of which is equal to or greater than another threshold value, as a significant radiographic image representative of the subject 42, rather than judging image data based on the average luminance value or variance luminance value of the image data. The average density value or variance density value may be an average or variance value of the entire image data, or an average or variance value of a particular area of the image data that represents the subject 42.

In the event that a radiographic image from the one radiation detecting device and a radiographic image from another radiation detecting device are acquired, the image judging section 157 may compare the two radiographic images (image data) with each other, and judge whether or not the two radiographic images are significant radiographic images representative of the subject 42.

Each of the cradles 32, 34, 36 comprises a controller 162, a transceiver 164, a charging processor 166, a display unit 168, and an ID memory 170.

The controllers 162 of the respective cradles 32, 34, 36 control components of the cradle 32, 34, 36 in their entirety.

The charging processors 166 charge the radiation detecting devices, which are connected to the cradles 32, 34, 36 outside the image capturing chambers 18, 20, 22. The transceivers 164 send signals to and receive signals from the transceivers 144 of the consoles 24, 26, 28.

Each of the controllers 162 stores the ID information of the radiation detecting device, which is currently being charged by the charging processor 166, in the ID memory 170. Each of the display units 168 displays information (charge level, ID information, etc.) of the radiation detecting device that is currently being charged. In a case that the cradle and radiation detecting device of the radiation detecting device are connected to each other, the controller 162 may read the ID information from the ID memory 132 of the radiation detecting device, and store the read ID information in the ID memory 170. Alternatively, the controller 162 may read ID information from a cradle thereof from the ID memory 146 of the console that is connected to a cradle of the console, and store the read ID information in the ID memory 170.

The radiographic image capturing system 10 according to the present embodiment is basically constructed as described above. Operations (a radiographic image capturing method) of the radiographic image capturing system 10 with an emphasis on the console 24 and the image capturing chamber 18 will be described below with reference to the flowchart shown in FIG. 5 and the timing chart shown in FIG. 6.

It is assumed that one radiation detecting device and one image capturing apparatus, which have been selected by the doctor or radiological technician in the image capturing chamber 18, are the radiation detecting device 72 and the image capturing apparatus 48, respectively, designed for an upright imaging process, whereas the other radiation detecting devices and the other image capturing apparatus are the radiation detecting device 62 and the image capturing apparatus 46, and the radiation detecting device 52 and the image capturing apparatus 44, respectively, which are designed for a supine imaging process. It is also assumed that, upon capturing of radiographic images, the power supply switches 94 are not turned on, but rather, the control device 40 activates the radiation detecting devices 52, 62, 72. It is further assumed that, after radiographic images have been captured, the control device 40 acquires the radiographic images preferentially from radiation detecting devices that are closer in proximity to the one radiation detecting device 72 (i.e., the control device 40 successively acquires radiographic images from the radiation detecting device 72, then from the radiation detecting device 62, and then from the radiation detecting device 52).

Figure 5:
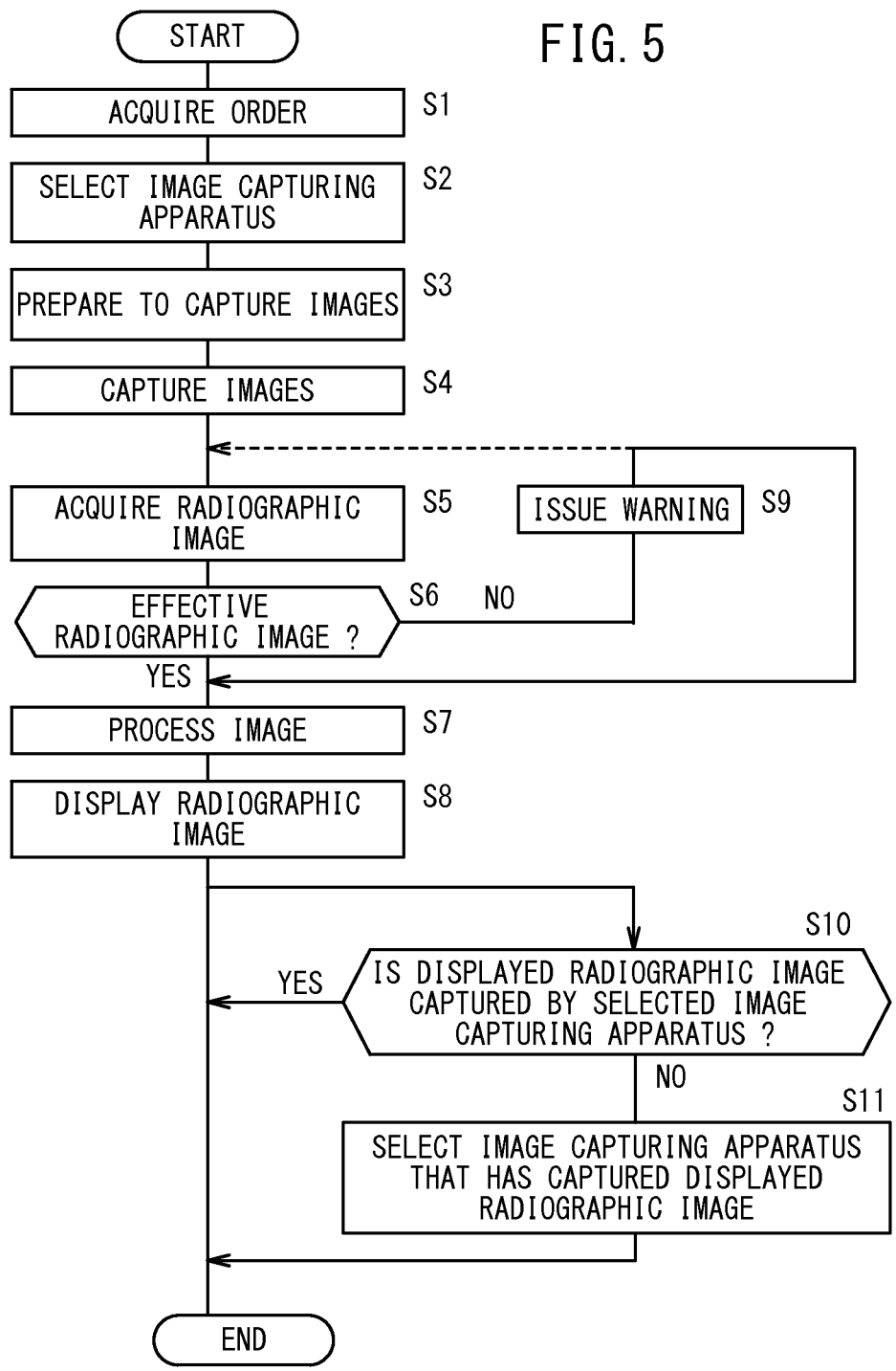
FIG. 5 is a flowchart of an operation sequence of the radiographic image capturing system according to the embodiment.
Figure 6:
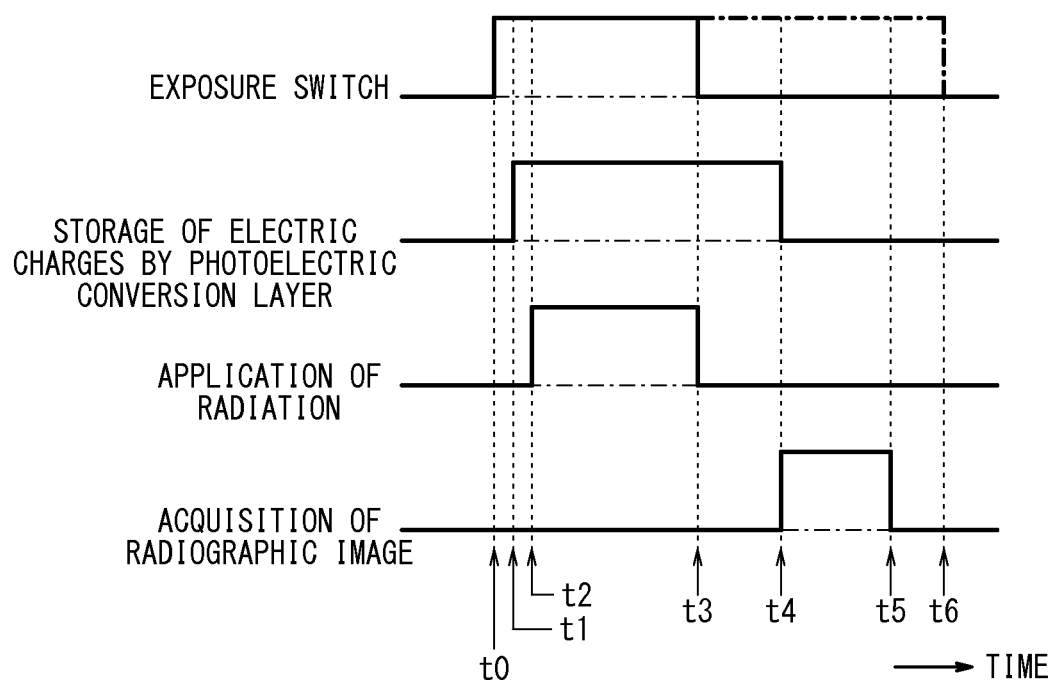
FIG. 6 is a timing chart showing an elapse of time from turning on of an exposure switch to completion of acquisition of a radiographic image.

In FIGS. 5 and 6, it is assumed that the one image capturing apparatus 48 initially performs an upright imaging process normally on the subject 42 according to the image capturing conditions, and thereafter, regardless of the image capturing conditions for the upright imaging process set in the image capturing condition setting section 150, the image capturing apparatus 46 performs a supine imaging process, instead of the upright imaging process performed by the image capturing apparatus 48.

First, operation of the one image capturing apparatus 48 in the image capturing chamber 18 to perform an upright imaging process normally on the subject 42 according to the image capturing conditions will be described below.

In step S1, the transceiver 144 of the console 24 acquires order information from the RIS 14 via the in-hospital network 30. The acquired order information is stored in the order information storage unit 148.

In step S2, the doctor or radiological technician operates the operating unit 159 of the console 24 in order to display the order information stored in the order information storage unit 148 on the display unit 156. Then, while observing the order information displayed on the display unit 156, the doctor or radiological technician operates the operating unit 159 in order to select the image capturing apparatus 48 to be used in the imaging process, to select an imaging method (upright imaging process) for the image capturing apparatus 48, and to enter the ID information of the radiation detecting device 72. The image capturing apparatus 48 and the imaging method that have been selected, the entered ID information, and the information contained within the order information, which corresponds to the selected and entered items of information, are set as image capturing conditions in the image capturing condition setting section 150. In addition, the doctor or radiological technician operates the operating unit 159 in order to enter ID information of all of the radiation detecting devices 52, 62, 72 that are present in the image capturing chamber 18, together with ID information of any radiation detecting devices that are currently being charged by the cradle 32 connected to the console 24. The entered ID information is stored in the ID memory 146.

In step S3, the doctor or radiological technician performs a preparatory process for making the selected image capturing apparatus 48 ready to capture radiographic images. More specifically, the doctor or radiological technician loads the image capturing base 70 with the radiation detecting device 72, the battery 88 of which has been charged by the cradle 32, and then positions the subject 42 with respect to the image capturing base 70. Further, the doctor or radiological technician orients the radiation source 54 toward the subject 42 and the image capturing base 70.

After the foregoing preparatory process has been completed, in step S4, the doctor or radiological technician turns on the exposure switch 160 in order to start an upright imaging process on the subject 42.

As shown in FIG. 6, upon the exposure switch 160 being turned on at time t0, the controller 142 sends the image capturing conditions set in the image capturing condition setting section 150, together with the ID information of the radiation detecting devices 52, 62, 72 stored in the ID memory 146, via the transceiver 144 to the transceiver 140 of the control device 40. The control device 40 stores the image capturing conditions and the ID information received by the transceiver 140 in the memory 138, and controls the radiation source 54 and the radiation detecting devices 52, 62, 72 according to the image capturing conditions and the ID information, so as to perform an upright imaging process on the subject 42 (irradiate the subject 42 with radiation 56).

Specifically, at time t1, the control device 40 controls the controller 90 via the transceivers 140, 92 in order to activate the radiation detecting devices 52, 62, 72. Under the control of the control device 40, the controller 90 supplies a bias voltage Vb from the battery 88 to the radiation conversion panel 84, thereby readying the pixels 100 for storage of electric charges therein.

At time t2, the control device 40 sends the image capturing conditions via the transceivers 140, 136 to the controller 134 of the radiation source 54. Based on the received image capturing conditions, the controller 134 outputs radiation 56 for a predetermined period (exposure time) from time t2 to time t3. Radiation 56 is applied through the subject 42 to the radiation detecting device 72 in the image capturing base 70. Then, radiation 56 that has passed through the subject 42 is directed toward the radiation conversion panel 84 in the radiation detecting device 72.

If the radiation detecting device 72 is an indirect-conversion-type radiation detecting device, then the scintillator of the radiation conversion panel 84 in the radiation detecting device 72 emits visible light at an intensity that depends on the intensity of the radiation 56. As described above, since the pixels 100 of the photoelectric conversion layer 101 are ready from time t1 for storing electric charges under the bias voltage Vb, the pixels 100 convert the visible light into electric signals, and store the electric signals as electric charges.

At time t4 when storage of electric charges in the pixels 100 is completed, the controller 90 supplies address signals to the line scanning driver 108 and the multiplexer 110, so as to start a process of reading the electric charge information representative of a radiographic image of the subject 42, which is held in the pixels 100.

More specifically, the address decoder 112 of the line scanning driver 108 outputs a selection signal according to the address signal supplied from the controller 90, so as to select one of the switches SW1, and the address decoder 112 supplies a control signal Von to the gates of the TFTs 106, which are connected to the gate line 102 corresponding to the selected switch SW1. The address decoder 118 of the multiplexer 110 outputs a selection signal according to the address signal output from the controller 90, so as to switch from one switch SW2 to another, and then successively reads, through the signal lines 104, radiographic images represented by electric charges held in the pixels 100, which are connected from the gate line 102 selected by the line scanning driver 108.

The radiographic images read from the pixels 100 connected to the gate line 102 are amplified by the respective amplifiers 114, and then are sampled by the sample and hold circuits 116. The radiographic images thus sampled are supplied through the multiplexer 110 to the A/D converter 120, which converts the radiographic images into digital signals. Such digital radiographic image signals are stored in the image memory 130 by the controller 90.

Similarly, the address decoder 112 of the line scanning driver 108 successively switches to other switches SW1 according to the address signal supplied from the controller 90. The radiographic images represented by electric charges held in the pixels 100, which are connected from the respective gate lines 102, are read through the signal lines 104 and stored in the image memory 130 through the multiplexer 110, the A/D converter 120, and the controller 90.

The image memory 130 thus stores a radiographic image which is representative of the subject 42 in an upright position. In step S4, the image capturing process of the image capturing apparatus 48 is carried out as has been described above. As with the radiation detecting device 72, the radiation detecting devices 52, 62 of the other image capturing apparatus 44, 46 also store electric charges therein and are capable of reading radiographic images. However, since radiation 56 is not applied to the radiation detecting devices 52, 62, the radiographic images read by the radiation detecting devices 52, 62 are not representative of the subject 42. From time t3 to time t4, the console 24 invalidates the function of the exposure switch 160 (inhibits application of radiation 56), even if the doctor or radiological technician turns on the exposure switch 160. Time t6 indicates a time at which the operation sequence concerning one image capturing cycle, which is represented by the flowchart shown in FIG. 5, is completed.

In step S5, after completion of the image capturing process, the control device 40 acquires via the controller 90 and the transceivers 92, 140 the radiographic image stored in the image memory 130 of the radiation detecting device 72 and the ID information stored in the ID memory 132, and sends the acquired radiographic image and ID information to the transceiver 144. After the radiographic image and the ID information from the radiation detecting device 72 have been sent to the transceiver 144, the control device 40 sends via the controller 90 and the transceivers 92, 140 the radiographic image stored in the image memory 130 of the radiation detecting device 62, which is close in proximity to the radiation detecting device 72, and the ID information stored in the ID memory 132 to the transceiver 144. Therefore, the transceiver 144 successively receives the ID information and the radiographic image from the radiation detecting device 72, as well as the ID information and the radiographic image from the radiation detecting device 62, and then stores the respective ID information and the radiographic images in the image memory 154.

In step S6, the image judging section 157 judges whether or not the radiographic image selected by the doctor or radiological technician from among the two radiographic images stored in the image memory 154 is a significant radiographic image representative of the subject 42.

As described above, since the image capturing apparatus 48 has imaged the subject 42 in an upright position and the radiographic image from the radiation detecting device 72 is representative of the subject 42, the average luminance value or variance luminance value of the radiographic image (image data) is equal to or greater than the threshold value. Inasmuch as the average luminance value or variance luminance value of the image data is equal to or greater than the threshold value, the image judging section 157 judges that the radiographic image from the radiation detecting device 72 is a significant radiographic image (step S6: YES), and further judges that the radiographic image from the radiation detecting device 62, which is stored in the image memory 154, is unnecessary.

Since the image judging section 157 has found a significant radiographic image, the image judging section 157 instructs the control device 40 to cancel the process of acquiring radiographic images, and erases the ID information and the radiographic image of the radiation detecting device 62 from the image memory 154. The image judging section 157 supplies the ID information and the radiographic image (significant radiographic image) of the radiation detecting device 72, which are stored in the image memory 154, to the image processor 152.

The image processor 152 performs a predetermined image processing routine on the supplied radiographic image from the radiation detecting device 72 (step S7), and displays the processed radiographic image on the display unit 156 (step S8).

In the period from time t4 to time t5, the process of acquiring radiographic images from the radiation detecting devices 52, 62, 72 is completed. The radiographic image displayed on the display unit 156 is sent through the in-hospital network 30 to the viewer 16 for interpretation and diagnosis thereof by the doctor.

An upright imaging process, which is performed normally on the subject 42 by the image capturing apparatus 48, has been described above.

A supine imaging process, which is performed by the image capturing apparatus 46 instead of the upright imaging process performed by the image capturing apparatus 48, regardless of the fact that the doctor or radiological technician has selected the image capturing apparatus 48 and the image capturing conditions for the image capturing apparatus 48 have been set in the image capturing condition setting section 150, will be described below.

In one instance, the doctor or radiological technician plans to perform an upright imaging process with the image capturing apparatus 48 according to the image capturing conditions, but due to a failure of the image capturing apparatus 48 or the radiation detecting device 72, the doctor or radiological technician determines instead to perform a supine imaging process, which is performed by the image capturing apparatus 46, instead of the upright imaging process performed by the image capturing apparatus 48. In another instance, if the imaging method is changed and a supine imaging process is performed by the image capturing apparatus 46, then it is presumed that the doctor or radiological technician should have operated the operating unit 159 to change the image capturing conditions registered in the image capturing condition setting section 150, but in fact, the doctor or radiological technician forgot to change the set image capturing conditions.

In step S3, the doctor or radiological technician loads the image capturing base 70 with the radiation detecting device 72, the battery 88 of which has been charged by the cradle 32. Then, the doctor or radiological technician positions the subject 42 with respect to the image capturing base 60, and orients the radiation source 54 toward the subject 42 and the image capturing base 60.

After completion of this preparatory process, in step S4, the doctor or radiological technician turns on the exposure switch 160 to initiate a supine imaging process on the subject 42.

Even though the image capturing apparatus 48 indicated by the image capturing conditions set in the image capturing condition setting section 150 and the image capturing apparatus 46 which actually performs the image capturing process are different from each other, and the doctor or radiological technician recognizes that a supine imaging process is to be performed by the image capturing apparatus 46, since the set image capturing conditions have not been changed, the console 24 recognizes that an image capturing process will be performed under the image capturing conditions (upright imaging process), which are currently set in the image capturing condition setting section 150.

As shown in FIG. 6, if the exposure switch 160 is turned on at time t0, the console 24 sends the image capturing conditions and the ID information of the radiation detecting devices 52, 62, 72, which are stored in the ID memory 146, to the control device 40. The control device 40 stores the received image capturing conditions and ID information in the memory 138, and controls the radiation source 54 and the radiation detecting devices 52, 62, 72 in accordance with the image capturing conditions and the ID information. The control device 40 controls the radiation source 54 and the radiation detecting devices 52, 62, 72, while recognizing that an upright imaging process is to be performed based on the image capturing conditions and the ID information.

At time t1, the control device 40 activates the radiation detecting devices 52, 62, 72, thereby readying the pixels 100 for storage of electric charges therein. At time t2, the control device 40 sends the image capturing conditions to the radiation source 54. The radiation source 54 irradiates the subject 42 with radiation 56 for a given exposure time from time t2 to time t3. Radiation 56 that has passed through the subject 42 is led to the radiation conversion panel 84 in the radiation detecting device 62. The scintillator of the radiation conversion panel 84 emits visible light at an intensity that depends on the intensity of the radiation 56. The pixels 100 convert the visible light into electric signals and store the electric signals as electric charges.

At time t4 when storage of electric charges in the pixels 100 is completed, the controller 90 supplies address signals to the line scanning driver 108 and the multiplexer 110 in order to initiate a process of reading the electric charge information held in the pixels 100, which is representative of a radiographic image of the subject 42, and the controller 90 stores the read radiation image in the image memory 130.

At this time, the image memory 130 of the radiation detecting device 62 stores the radiographic image, which is representative of the subject 42 in a supine position. Therefore, the radiographic image from the radiation detecting device 72, which has been selected by the doctor or radiological technician, and the radiographic image from the other radiation detecting device 52 are not representative of the subject 42.

In step S5, the control device 40 acquires the ID information and the radiographic image from the radiation detecting device 72, and sends the ID information and the radiographic image to the transceiver 144. Thereafter, the control device 40 acquires the radiographic image and the ID information from the radiation detecting device 62, and sends the radiographic image and the ID information to the transceiver 144.

In step S6, the image judging section 157 judges whether or not the radiographic image selected by the doctor or radiological technician from the two radiographic images stored in the image memory 154 is a significant radiographic image representative of the subject 42.

As described above, inasmuch as the image capturing apparatus 46 has captured a radiographic image of the subject 42 in a supine position, the radiographic image from the radiation detecting device 72 is not representative of the subject 42, and hence the average luminance value or variance luminance value of the radiographic image (image data) is smaller than the threshold value. Therefore, the image judging section 157 determines that the radiographic image from the radiation detecting device 72 is not a significant radiographic image (step S6: NO). The image judging section 157 then determines whether or not the radiographic image from the radiation detecting device 62 is a significant radiographic image representative of the subject 42.

Since the radiographic image from the radiation detecting device 62 is representative of the subject 42, and hence the average luminance value or variance luminance value of the image data thereof is equal to or greater than the threshold value, the image judging section 157 determines that the radiographic image from the radiation detecting device 72 is a significant radiographic image. In order to indicate to the radiological technician that the radiographic image according to the image capturing conditions (the radiographic image obtained from the image capturing apparatus 48 in the upright imaging process) and the actually produced radiographic image (the radiographic image obtained from the image capturing apparatus 46 in the supine imaging process) do not agree with each other, the image judging section 157 produces an audible speech warning through the speaker 158 and/or displays a visual warning through the display unit 156 (step S9).

Inasmuch as the radiographic image from the radiation detecting device 62 is a significant radiographic image, the image judging section 157 judges as unnecessary the radiographic image from the radiation detecting device 72, which is stored in the image memory 154. Since the image judging section 157 has found the significant radiographic image, the image judging section 157 instructs the control device 40 to cancel the process of acquiring radiographic images, and erases the ID information and the radiographic image of the radiation detecting device 72 from the image memory 154. The image judging section 157 supplies the ID information and the radiographic image (significant radiographic image) of the radiation detecting device 62 to the image processor 152.

The image processor 152 performs a predetermined image processing routine on the supplied radiographic image from the radiation detecting device 62 (step S7), and displays the processed radiographic image on the display unit 156 (step S8).

The image judging section 157 also is capable of judging whether or not the radiographic image displayed on the display unit 156 is a radiographic image captured by the image capturing apparatus 48 under the image capturing conditions (step S10). As described above, since the radiographic image displayed on the display unit 156 is a radiographic image captured by the image capturing apparatus 46, which is different from the image capturing apparatus 48 represented by the image capturing conditions (step S10: NO), the image judging section 157 changes the image capturing conditions for the image capturing apparatus 48, which are currently set in the image capturing condition setting section 150, into image capturing conditions for the image capturing apparatus 46, based on the assumption that a next radiographic image will be captured by the image capturing apparatus 46 that has captured the radiographic image displayed on the display unit 156 (step S11). As a result, the image capturing apparatus 46 will be selected for capturing a subsequent radiographic image, thereby preventing the image capturing apparatus 46 from being unselected due to an oversight.

A supine imaging process, which is carried out by the image capturing apparatus 46 instead of the upright imaging process carried out by the image capturing apparatus 48, has been described above.

If a supine imaging process is performed using the image capturing apparatus 44 instead of using the image capturing apparatus 46, then after having issued a warning in step S9, the image judging section 157 instructs the control device 40 to acquire the ID information and the radiographic image from the radiation detecting device 52 of the image capturing apparatus 44. Control then returns to step S5, in which the control device 40 is instructed by the image judging section 157 to acquire the ID information and the radiographic image from the radiation detecting device 52, and the control device 40 sends the ID information and the radiographic image, which have been acquired, to the console 24. Therefore, the image judging section 157 performs the process from step S6 again.

According to the present embodiment, as described above, the control device 40 acquires both the radiographic image from one radiation detecting device (one image capturing apparatus), which is selected by the doctor or radiological technician by operating the operating unit 159, and the radiographic image from at least one other radiation detecting device (other image capturing apparatus) that differs from the one radiation detecting device, and the control device 40 sends the acquired radiographic images to the consoles 24, 26, 28.

If radiation 56 is applied through the subject 42 to the one radiation detecting device, then the control device 40 acquires a radiographic image from the one radiation detecting device, thereby acquiring a radiographic image representative of the subject 42. If radiation 56 is applied through the subject 42 to the other radiation detecting device, then the control device 40 acquires a radiographic image from the other radiation detecting device, thereby acquiring a radiographic image representative of the subject 42.

More specifically, in a case that the one image capturing apparatus is changed to the other image capturing apparatus in order to capture a radiographic image, it is desirable for the doctor or radiological technician to operate the operating unit 159, so as to select the other image capturing apparatus before the radiographic image is captured. However, the doctor or radiological technician may possibly fail to select the other image capturing apparatus for capturing a radiographic image, and thus a radiographic image may not be acquired from the other image capturing apparatus. According to the present embodiment, regardless of whether or not the doctor or radiological technician has actively operated the operating unit 159 in order to select the other image capturing apparatus, both the radiographic image from the one radiation detecting device and the radiographic image from the other radiation detecting device are acquired, thereby reliably acquiring a radiographic image representative of the subject 42.

According to the present embodiment, therefore, regardless of whether or not the one radiation detecting device or the other radiation detecting device has been used to capture a radiographic image, the control device 40 reliably acquires a radiographic image that is representative of the subject 42. As a result, the subject 42 is prevented from being exposed to radiation 56 needlessly.

The image judging section 157 of each of the consoles 24, 26, 28 judges whether or not the radiographic image from the one radiation detecting device is a significant radiographic image representative of the subject 42. Therefore, it is possible to determine whether or not the radiographic image from the one radiation detecting device is a significant radiographic image representative of the subject 42.

If the image judging section 157 determines that the radiographic image from the one radiation detecting device is not a significant radiographic image, then the image judging section 157 issues a warning through the speaker 158 and/or the display unit 156. Therefore, the doctor or radiological technician can easily recognize that an image capturing process has been carried out, without being required to operate the operating unit 159 in order to select the other radiation detecting device.

If the image judging section 157 determines that the radiographic image from the one radiation detecting device is not a significant radiographic image, then the image judging section 157 judges whether or not the radiographic image from the other radiation detecting device is a significant radiographic image. Therefore, it is possible to determine whether or not the radiographic image from the other radiation detecting device is a significant radiographic image.

If the image judging section 157 determines that the radiographic image from the one radiation detecting device is not a significant radiographic image, then the control device 40 successively acquires radiographic images from the other radiation detecting devices until the image judging section 157 finds a significant radiographic image. Therefore, a significant radiographic image can reliably be acquired.

According to the present embodiment, in the event that the doctor or radiological technician operates the operating unit 159 in order to select the one radiation detecting device, the doctor or radiological technician also designates an imaging method to be carried out at the time that radiation 56 is applied to the subject 42 using the one radiation detecting device. In this case, the control device 40 acquires a radiographic image preferentially from a radiation detecting device, from among the other radiation detecting devices, which produces a radiographic image according to the imaging method, or acquires a radiographic image preferentially from another radiation detecting device that is close in proximity to the one radiation detecting device.

If the one radiation detecting device is not used, but rather another radiation detecting device is used to capture a radiographic image, then it is assumed to be highly likely to have captured a radiographic image using another radiation detecting device, according to the same imaging method as the imaging method (e.g., upright imaging process or supine imaging process) of the one radiation detecting device, or to have captured a radiographic image using another radiation detecting device that is closest in proximity to the one radiation detecting device. The control device 40 thus acquires a radiographic image preferentially from another radiation detecting device according to the same imaging method, or from another radiation detecting device that is closest in proximity to the one radiation detecting device. Consequently, it is possible to acquire a significant radiographic image quickly and reliably.

For example, if radiographic images are to be acquired according to imaging methods, then the radiographic images may be acquired according to the following sequence. Assuming that the one radiation detecting device is the radiation detecting device 72, then radiographic images are acquired according to a sequence in which the radiation detecting device 72 in the upstanding imaging process→the radiation detecting device 62 in the supine imaging process→the radiation detecting device 52 (in the supine imaging process) are selected in this order. Assuming that the one radiation detecting device is the radiation detecting device 62, then radiographic images are acquired according to a sequence in which the radiation detecting device 62 in the supine imaging process→the radiation detecting device 52 (in the supine imaging process)→the radiation detecting device 72 in the upstanding imaging process are selected in this order.

If the image judging section 157 determines that the radiographic image from the other radiation detecting device is a significant radiographic image, then the image judging section 157 switches from the image capturing conditions for the one radiation detecting device, which are set in the image capturing condition setting section 150 (selection of the one radiation detecting device), to the image capturing conditions for the other radiation detecting device (selection of the other radiation detecting device). In this case, since it is assumed that a subsequent imaging cycle will be carried out using the other radiation detecting device, which has produced the significant radiographic image, the image judging section 157 automatically switches from selecting the one radiation detecting device to selecting the other radiation detecting device, thereby preventing the other radiation detecting device from being unselected due to an oversight in the next imaging cycle.

Each of the consoles 24, 26, 28 displays, on the display unit 156, the radiographic image that the image judging section 157 has judged as being a significant radiographic image. Accordingly, the doctor can interpret the significant radiographic image for facilitating diagnosis.

Since the ID memory 146 stores ID information of all of the radiation detecting devices 52, 62, 72 that are present in the image capturing chambers 18, 20, 22, the control device 40 stores the ID information in the ID memory 146 in the memory 138, and thereafter acquires radiographic images from the radiation detecting devices 52, 62, 72 that are present in the image capturing chambers 18, 20, 22 according to such ID information and the image capturing conditions.

Inasmuch as radiographic images are acquired only from the radiation detecting devices 52, 62, 72 that are present in the image capturing chambers 18, 20, 22, it is possible to reliably prevent an image acquiring process from being performed in error using radiation detecting devices that are present outside of the image capturing chambers 18, 20, 22, e.g., radiation detecting devices that are currently being charged by the cradles 32, 34, 36 and radiation detecting devices in image capturing chambers in which radiographic images are not being captured. Further, the process of acquiring radiographic images can be carried out efficiently.

Since each radiation conversion panel 84 is made ready to store electric charges before radiation 56 is applied to the subject 42, it is not necessary to irradiate the radiation detecting devices 52, 62, 72 with triggering radiation 56 in order to instruct the radiation conversion panel 84 to store electric charges therein prior to the main image capturing process. Therefore, the arrangement for instructing the storage of electric charges is simplified, and the dose of radiation to which the subject 42 is exposed can be reduced.

In the above description, the control device 40 and the consoles 24, 26, 28 are separate from each other. However, the control device 40 may be dispensed with, and the function of the control device 40 to acquire radiographic images may be possessed by the controller 142.

If the subject 42 to be imaged is thick bodied, then the dose of radiation 56 that reaches the radiation detecting device, which is used to capture a radiographic image, may possibly be smaller than the dose of radiation that leaks to other radiation detecting devices. According to the present embodiment, therefore, correlative data between mAs values together with the thickness of the subject 42, and patterns of radiographic images produced upon leakage of radiation may be registered in advance in the image capturing condition setting section 150. In this case, a radiographic image, which is generated from a thick bodied subject, may be corrected using such registered data and patterns.

It has been described above that a doctor or radiological technician operates the operating unit 159 in order to register an imaging method in the image capturing condition setting section 150, whereupon the doctor or radiological technician orients the radiation source 54 toward the subject 42 in a preparatory process. However, according to the present embodiment, the present invention is not limited to such details in the preparatory process. Imaging methods and movements of the radiation source 54 may be associated with each other, and in the event that an imaging method is registered in the image capturing condition setting section 150, the radiation source 54 may be automatically moved in accordance with the imaging method. Alternatively, in the event that the radiation source 54 is moved in the preparatory process, an imaging method, which depends on the moved radiation source 54, may automatically be registered in the image capturing condition setting section 150.

Furthermore, if an imaging method is changed from the image capturing apparatus 48 to the image capturing apparatus 46, the dose of radiation 56 according to the image capturing conditions may be changed depending on the changed imaging method, and the changed dose of radiation 56 may be output from the radiation source 54.

The present invention is not limited to the embodiment described above, but various changes and modifications may be made without departing from the scope of the invention.

The invention claimed is:

1. A radiographic image capturing system comprising:
a plurality of radiographic image capturing apparatus that are disposed in one image capturing chamber and are used for capturing images of a subject in a supine position or an upright position, a radiation source which outputs radiation based on an image capturing condition being shared by said plurality of image capturing apparatuses and being movable towards the subject, said plurality of radiographic image capturing apparatuses including
respective radiation detecting devices each of which is placed on or in an image capturing base and converts the radiation having passed through the subject into a radiographic image; and
a radiographic image acquiring apparatus including
a selector configured to select one radiation detecting device of one radiographic image capturing apparatus from among the radiation detecting devices of the plurality of radiographic image capturing apparatus,
an acquirer configured to acquire, based on an image capturing condition for the one radiation detecting device, a radiographic image from the one radiation detecting device and a radiographic image from another radiation detecting device which is at least one different radiation detecting device of another radiographic image capturing apparatus that differs from the one radiation detecting device, from among the radiation detecting devices of the plurality of radiographic image capturing apparatus, in a case that a subject is irradiated with the radiation,
a judging section configured to judge whether or not the radiographic image from the one radiation detecting device is a significant radiographic image representative of the subject and judge whether or not the radiographic image from another radiation detecting device is a significant radiographic image in a case that the radiographic image from the one radiation detecting device is not a significant radiographic image, wherein the judging includes obtaining a significance value of a radiographic image and determining whether the significance value indicates that the radiographic image is representative of the subject, and a switcher configured to switch from the image capturing condition for the one radiation detecting device to an image capturing condition for the different detecting device, if the judging section judges that the radiographic image from the different radiation detecting device is the significant radiographic image.

2. The radiographic image acquiring apparatus according to claim 1, further comprising:
an indicating unit for externally indicating a judgment result from the judging section, if the judging section judges that the radiographic image from the one radiation detecting device is not the significant radiographic image.

3. The radiographic image acquiring apparatus according to claim 1, wherein the judging section judges whether or not the radiographic image from the other radiation detecting device is the significant radiographic image, if the judging section judges that the radiographic image from the one radiation detecting device is not the significant radiographic image.

4. The radiographic image acquiring apparatus according to claim 1, wherein the acquirer successively acquires radiographic images from other radiation detecting devices until the judging section has found the significant radiographic image, if the judging section judges that the radiographic image from the one radiation detecting device is not the significant radiographic image.

5. The radiographic image acquiring apparatus according to claim 4, wherein the selector selects the one radiation detecting device, and designates an imaging method to be carried out upon application of radiation to the subject using the one radiation detecting device; and the acquirer acquires a radiographic image preferentially from a radiation detecting device, from among the other radiation detecting devices, which produces a radiographic image according to the imaging method, or acquires a radiographic image preferentially from another radiation detecting device that is in close proximity to the one radiation detecting device.

6. The radiographic image acquiring apparatus according to claim 1, further comprising:
an output unit for externally outputting the radiographic image which the judging section has judged as being the significant radiographic image.

7. The radiographic image acquiring apparatus according to claim 1, wherein in a case that the radiation is applied to the subject in an image capturing chamber, the acquirer acquires the radiographic image from the one radiation detecting device and the radiographic image from the other radiation detecting device, which also is present in the image capturing chamber, from among the plurality of radiation detecting devices.

8. The radiographic image acquiring apparatus according to claim 1, further comprising:
an identification information storage unit for storing identification information of the plurality of radiation detecting devices that are present in the image capturing chamber in a case that the radiation is applied to the subject in the image capturing chamber,
wherein the acquirer acquires radiographic images from the plurality of radiation detecting devices that are present in the image capturing chamber based on the identification information stored in the identification information storage unit.

9. The radiographic image acquiring apparatus according to claim 1, wherein each of the radiation detecting devices comprises a radiation conversion panel for converting the radiation into electric charges, storing the electric charges, and outputting the stored electric charges as an electric signal to an external device, and the radiation conversion panel is made ready to store the electric charges before the radiation is applied to the subject.

* * * * *